(12) United States Patent
Kumar et al.

(10) Patent No.: US 9,080,001 B2
(45) Date of Patent: Jul. 14, 2015

(54) FLAME-RETARDANT DERIVATIVES

(75) Inventors: Jayant Kumar, Westford, MA (US); E. Bryan Coughlin, Amherst, MA (US); Todd Emrick, South Deerfield, MA (US); Bon-Cheol Ku, Wanju-gun (KR); Sethumadhavan Ravichandran, Marlborough, MA (US); Subhalakshmi Nagarajan, Sheffield Village, OH (US); Ramaswamy Nagarajan, Westford, MA (US); Weeradech Kiratitanavit, Lowell, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/115,165

(22) PCT Filed: Apr. 30, 2012

(86) PCT No.: PCT/US2012/035802
§ 371 (c)(1),
(2), (4) Date: Feb. 24, 2014

(87) PCT Pub. No.: WO2012/151154
PCT Pub. Date: Nov. 8, 2012

(65) Prior Publication Data
US 2014/0155569 A1 Jun. 5, 2014

Related U.S. Application Data

(60) Provisional application No. 61/481,414, filed on May 2, 2011.

(51) Int. Cl.
*C08G 8/02* (2006.01)
*C07C 49/83* (2006.01)
*C07C 49/84* (2006.01)
*C12P 7/26* (2006.01)

(52) U.S. Cl.
CPC . *C08G 8/02* (2013.01); *C07C 49/83* (2013.01); *C07C 49/84* (2013.01); *C12P 7/26* (2013.01)

(58) Field of Classification Search
USPC .......................... 528/125; 568/331; 435/148
See application file for complete search history.

(56) References Cited

U.S. PATENT DOCUMENTS

| 4,668,739 A | 5/1987 | Berdahl et al. |
| 4,883,856 A | 11/1989 | Petri |

(Continued)

FOREIGN PATENT DOCUMENTS

| WO | WO 2009/123969 A2 | 10/2009 |
| WO | WO 2012/151154 A2 | 11/2012 |

OTHER PUBLICATIONS

TerHaar, G.L., "Product stewardship in the flame retardant industry" *Fire Mater.* 28:417-421 (2004).

(Continued)

*Primary Examiner* — Shane Fang
(74) *Attorney, Agent, or Firm* — Hamilton, Brook, Smith & Reynolds, P.C.

(57) ABSTRACT

A chemical compound of structural formula (I) useful in preparation of flame retardant materials is disclosed. Homopolymer, and copolymers of a compound of formula (I), as well as methods of preparing said homo- and copolymers are also disclosed. Polymers described herein advantageous possess low heat release capacities and high char yields.

7 Claims, 10 Drawing Sheets $R_1 = OH, R_2 = OH, R_3 = R_4 = R_5 = R_6 = H;$   1
$R_1 = OH, R_2 = OCH_3, R_3 = R_4 = R_5 = R_6 = H;$   2
$R_1 = OH, R_2 = OH, R_3 = R_4 = R_5 = R_6 = C_5\text{-}C_8 \text{ chain};$   3
$R_1 = OH, R_2 = OCH_3, R_3 = R_4 = R_5 = R_6 = C_5\text{-}C_8 \text{ chain};$   4
$R_1 = OH, R_2 = OH, R_3 = R_4 = R_5 = R_6 = CH_3;$   5
$R_1 = OH, R_2 = OCH_3, R_3 = R_4 = R_5 = R_6 = CH_3;$   6

Here,
1 - 4,4'-Bishydroxydeoxybenzoin (BHDB)
2 - 4-methoxy,4'-hydroxydeoxybenzoin(MHDB)

(56) References Cited

U.S. PATENT DOCUMENTS

| | | | |
|---|---|---|---|
| 5,089,595 | A | 2/1992 | Petri |
| 6,018,018 | A | 1/2000 | Samuelson et al. |
| 6,569,651 | B1 | 5/2003 | Samuelson et al. |
| 6,689,465 | B1 * | 2/2004 | Omori et al. ............. 428/402 |
| 7,202,030 | B2 | 4/2007 | Dordick et al. |
| 7,223,432 | B2 | 5/2007 | Cholli et al. |
| 7,507,454 | B2 | 3/2009 | Cholli et al. |
| 7,863,400 | B2 | 1/2011 | Emrick et al. |
| 2003/0225132 | A1 | 12/2003 | Dininno et al. |
| 2008/0033144 | A1 | 2/2008 | Emrick et al. |
| 2013/0102754 | A1 * | 4/2013 | Emrick et al. ............. 528/125 |

OTHER PUBLICATIONS

Lassen, C., et al., Brominated Flame Retardants, Substance Flow Analysis and Assessment of Alternatives, 221 Danish Environmental Protection Agency [online] Jun. 1999 [retrieved on Apr. 15, 2014]. Retrieved from the Internet URL:http://www2.mst.dk/udgiv/Publications/1999/87-7909-416-3/html/kap01_eng.htm.

Bruno, F.F., et al., "Polymerization of water-soluble conductive polyphenol using horseradish peroxidase" *J. Macromol. Sci.—Part A: Pure Appl. Chem.*, 38(12):1417-1426 (2001).

van der Waals, A.C.L.M., et al., "Novel dehydration of stilbene oxides to diphenylacetylene using flash vacuum thermolysis with solid acid catalysts," *J. Mol. Catal. A Chem.*, 134:179-189 (1998).

Ellzey, K.A., et al., "Deoxybenzoin-Based Polyarylates as Halogen-Free Fire-Resistant Polymers," *Macromolecules*, 39:3553-3558 (2006).

Ranganathan, T., et al., "Synthesis and Characterization of Halogen-Free Antiflammable Polyphosphonates Containing 4,4'-Bishydroxydeoxybenzoin," *Macromolecules*, 39:5974-5975 (2006).

International Preliminary Report on Patentability in International Application No. PCT/US2012/035802, "Flame-Retardant Derivatives," mailed Nov. 14, 2013.

International Search Report and The Written Opinion in International Application No. PCT/US2012/035802, "Flame-Retardant Derivatives," date of mailing Dec. 26, 2012.

* cited by examiner

FIG. 8: FTIR-ATR analysis of cardanol monomer and poly(cardanol) synthesized using K3 [Fe(CN)

FLAME-RETARDANT DERIVATIVES

RELATED APPLICATIONS

This application is the U.S. National Stage of International Application No. PCT/US2012/035802, filed Apr. 30, 2012, which designates the U.S., published in English, and claims the benefit of U.S. Provisional Application No. 61/481,414, filed May 2, 2011. The entire teachings of the above applications are incorporated herein by reference.

GOVERNMENT SUPPORT

This invention was made with government support under Grant #13004 awarded by the Toxic Use Reduction Institute, Grant #99-G-035 awarded by Federal Aviation Administration, and Grant #60NANB6D6123, awarded by National Institute of Standards and Technology. The government has certain rights in the invention.

BACKGROUND OF THE INVENTION

Flame retardant (FR) materials control or reduce the risk of fire and therefore have a direct impact on safety. Flame-retardant additives are often needed as a component of finished commercial products and, more specifically organic/polymer based materials. Approximately 909,000 tons/year of flame retardant additives are used in the polymer industry alone to make them less flammable.

Flame initiation and subsequent propagation through a material can happen in several different ways. Propagation of flame through the polymer backbone is often preceded by the formation of extremely reactive OH and H radicals. Most halogenated FRs act by the abstraction of these highly reactive radicals. Other flame retardants, including some metal oxides, work on the principle of generating char, forming a protective layer on the surface, which starves oxygen supply to the interior layer, facilitating flame quenching. The use of halogenated flame retardants is convenient and popular because of its good compatibility with polymer systems, easy processability and very efficient fire retardancy.

In the polymer industry, flame retardancy is often achieved by blending polymers with flame retardant additives, such as halocarbons, including polybrominated diphenyl ether (PBDE), phosphorous, organophosphates and metal oxides. While small molecule flame-retardant additives provide a convenient means for reducing flammability of materials, these additives may compromise safety from environmental and health perspectives. Conventional FRs are small molecule additives that often leach out of the polymer during their use leading to a variety of serious health and environmental problems associated with toxicity and bioaccumulation. Halogenated compounds are linked to detrimental effects on the nervous system. The presence of trace amounts of PBDEs in sperm whales, seals, dolphins and even the human population, poses enormous environmental threat and health related issues throughout the world. With the European Union banning the use of halogenated FR, there has been a tremendous need for the development of environmentally friendly, non toxic, low leaching alternative halogen free FR polymers and additives.

SUMMARY OF THE INVENTION

In one embodiment, the present invention is a chemical compound of structural formula (I):

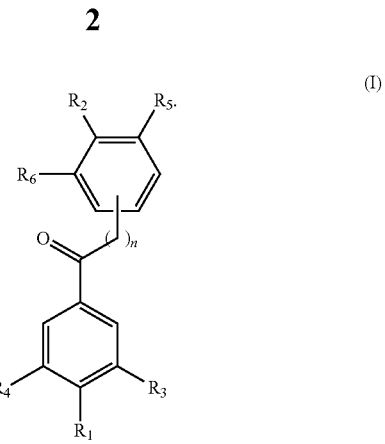

In formula (I), $R^1$, $R^2$, $R^3$, $R^4$, $R^5$ and $R^6$ each independently is selected from —H, —OH, a C1-C8 alkoxy, a C1-C15 alkyl, a C2-C15 alkenyl or a C2-C15 alkynyl; and n is 0 or 1. In exemplary embodiments, (1) at least one of $R^1$, $R^2$, $R^3$, $R^4$, $R^5$ and $R^6$ is —OH; (2) when n=1 and when $R^1$ and $R^2$ each is —OH, then at least one of $R^3$, $R^4$, $R^5$ and $R^6$ is not —H; and (3) when $R^1$ is —OH and $R^2$ is —OCH$_3$, then at least one of $R^3$, $R^4$, $R^5$ and $R^6$ is not —H.

In other embodiments, the present invention is a poly(hydroxydeoxybenzoin) homopolymer of any one of the monomers of structural formula (I). In exemplary embodiments, at least one of $R^1$, $R^2$, $R^3$, $R^4$, $R^5$ and $R^6$ is —OH.

In other embodiments, the present invention is a poly(hydroxydeoxybenzoin) copolymer of at least one of the monomers of structural formula (I) and at least one additional monomer. In exemplary embodiments, (1) at least one of $R^1$, $R^2$, $R^3$, $R^4$, $R^5$ and $R^6$ is —OH; and (2) when n=1 and when $R^1$ and $R^2$ each is —OH, then at least one of $R^3$, $R^4$, $R^5$ and $R^6$ is not —H.

In other embodiments, the present invention is a method of producing a poly(hydroxydeoxybenzoin) homopolymer of any one of the monomers of structural formula (I) comprising the step of synthesizing a covalent bond between at least two monomers of structural formula (I) to produce the poly(hydroxydeoxybenzoin) homopolymer. In exemplary embodiments, at least one of $R^1$, $R^2$, $R^3$, $R^4$, $R^5$ and $R^6$ is —OH.

In other embodiments, the present invention is a method of producing a poly(hydroxydeoxybenzoin) copolymer of at least one of the monomers of structural formula (I) and at least one additional monomer comprising the step of synthesizing a covalent bond between at least one monomer of structural formula (I) and at least one additional monomer to produce the poly(hydroxydeoxybenzoin) copolymer. In exemplary embodiments, (1) at least one of $R^1$, $R^2$, $R^3$, $R^4$, $R^5$ and $R^6$ is —OH; and (2) when n=1 and when $R^1$ and $R^2$ each is —OH, then at least one of $R^3$, $R^4$, $R^5$ and $R^6$ is not —H.

In other embodiments, the present invention is an article of manufacture, comprising a poly(hydroxydeoxybenzoin) homopolymer of any one of the monomers of structural formula (I). In exemplary embodiments, at least one of $R^1$, $R^2$, $R^3$, $R^4$, $R^5$ and $R^6$ is —OH.

In other embodiments, the present invention is an article of manufacture, comprising a poly(hydroxydeoxybenzoin) copolymer of at least one of the monomers of structural formula (I) and at least one additional monomer. In exemplary embodiments, (1) at least one of $R^1$, $R^2$, $R^3$, $R^4$, $R^5$ and $R^6$ is —OH; and (2) when n=1 and when $R^1$ and $R^2$ each is —OH, then at least one of $R^3$, $R^4$, $R^5$ and $R^6$ is not —H.

The substituted phenols, and homo- and copolymers of the substituted phenols of the present invention possess enhanced thermal stability, flame retardant (FR) and antioxidant properties. The homo- and copolymers of the present invention are thermally stable with very low heat release, comparable or lower than Nomex™. The polymers described herein can be used in textile and fabric industries, automotive and household upholstery, electronics and aviation industries, automotive and structural components, etc.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
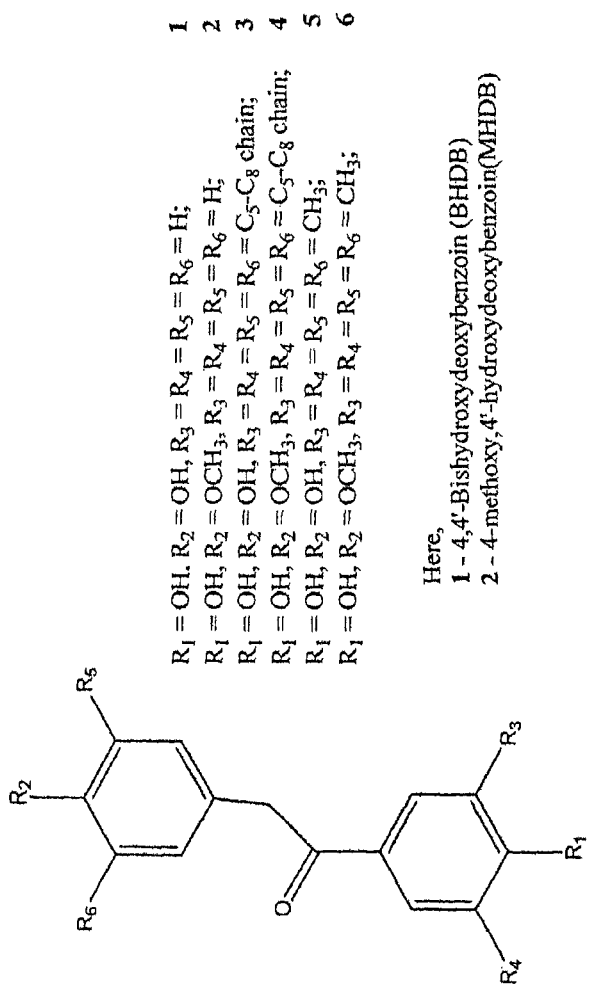
FIG. 1 is an illustration of exemplary monomers of the present invention.

There is a need for a non-halogenated flame retardant, preferably with the use of enzymatic synthetic methods, under mild aqueous reaction conditions. Substituted phenolic monomers described herein were selected due to their properties described below.

In one embodiment, the present invention is a method of synthesis of homo- and copolymers of phenol derivatives that employs oxidation catalysts. The method employs naturally occurring enzymes for the synthesis of a new class of polymeric phenols with enhanced thermal stability, low heat release capacity [HRC] (comparable to Nomex™) and high char forming capability for novel fire retardant (FR) applications. A variety of monomers can also be copolymerized to improve yields, solubility and processability of the FR polymers. Co-polymerization of these monomers with phenolic entities increases the yield of these reactions. The oligomers synthesized are processable and soluble in common organic solvents.

A description of example embodiments of the invention follows.

The term "alkyl", as used herein, unless otherwise indicated, includes saturated monovalent hydrocarbon chains having straight or branched moieties, typically C1-C16, preferably C1-C12. Examples of alkyl groups include, but are not limited to, methyl, ethyl, propyl, isopropyl, and t-butyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond wherein alkyl is as defined above. Examples of alkynyl groups include, but are not limited to, ethynyl and 2-propynyl.

The terms "alkoxy", as used herein, means an "alkyl-O-" group, wherein alkyl, is defined above.

Alkyl, alkenyl and alkynyl groups, as well as the alkyl portion of the alkoxy groups included in compounds of this invention may be optionally substituted with one or more substituents. Examples of suitable substituents include —OH, —SH, halogen, amino, cyano, a C1-C12 alkyl, C1-C12 haloalkyl, C1-C12 alkoxy, or C1-C12 haloalkoxy.

As used herein, an amino group may be a primary ($-NH_2$), secondary ($-NHR_x$), or tertiary ($-NR_xR_y$), wherein $R_x$ and $R_y$ may be any of the optionally substituted alkyls described above.

As used herein, the term "halogen" means F, Cl, I or Br.

The term "heme-containing enzyme," as used herein, means an enzyme having an iron in the catalytic active site and wherein the catalytic site includes a heme group. Examples of heme-containing enzymes include peroxidases, ligninases and catalases.

The term "metalloporphyrin-containing enzyme," as used herein, means an enzyme having a native porphyrin with a metal center in the catalytic site, without globular protein residues, defined as proteins residues that are water soluble. Examples of metalloporphyrin-containing enzymes include hemoglobin, myoglobin, cytochromes and rubredoxins.

In one embodiment, the present invention is a chemical compound of structural formula (I):

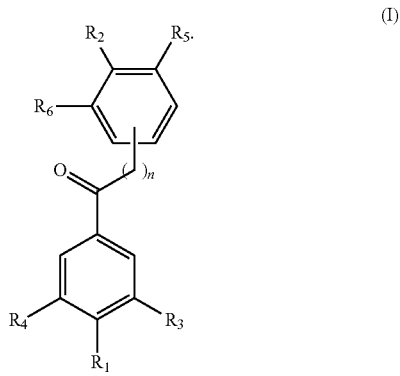

In formula (I), $R^1$, $R^2$, $R^3$, $R^4$, $R^5$ and $R^6$ each independently is selected from —H, —OH, a C1-C8 alkoxy, a C1-C15 alkyl, a C2-C15 alkenyl or a C2-C15 alkynyl and n is 0 or 1.

In certain embodiments, $R^1$, $R^2$, $R^3$, $R^4$, $R^5$ and $R^6$ each independently is selected from —H, —OH, a C1-C8 alkoxy, a C1-C15 alkyl. In certain embodiments at least one of $R^1$, $R^2$, $R^3$, $R^4$, $R^5$ and $R^6$ is —OH. On other embodiments, $R^1$ and $R^2$ each is —OH, then at least one of $R^3$, $R^4$, $R^5$ and $R^6$ is not —H. In yet other embodiments, when $R^1$ is —OH and $R^2$ is —OCH$_3$, then at least one of $R^3$, $R^4$, $R^5$ and $R^6$ is not —H.

Exemplary embodiments of the compound of formula (I) are compounds represented by a structural formula selected from formulas (II), (III) and (IV):

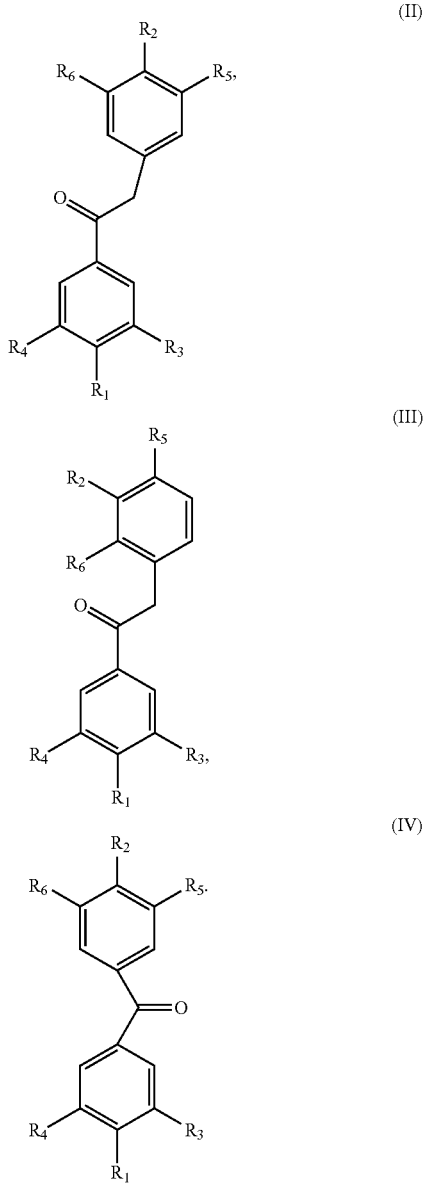

In formulas (II), (III) and (IV) the values and preferred values of the variables are as defined with respect to formula (I).

In certain embodiments of the compounds of formulas (I) through (IV), $R^1$ is —OH and $R^2$ is —OH or —OCH$_3$. Values and preferred values of the remainder of the variables are as defined with respect to formula (I).

In certain embodiments of the compounds of formulas (I) through (IV), $R^1$ is —OH and $R^2$ is —OH or —OCH$_3$ and $R^3$, $R^4$, $R^5$ and $R^6$ each is independently —H or a C1-C8 alkyl. Values and preferred values of the remainder of the variables are as defined with respect to formula (I).

In certain embodiments of the compounds of formulas (I) through (IV), $R_1$ is —OH, $R_2$ is —OH, and $R_3$, $R_4$, $R_5$, and $R_6$ each is each independently a C5-C8 alkyl, or $R_1$ is —OH, $R_2$ is —OCH$_3$, and $R_3$, $R_4$, $R_5$, and $R_6$ each is each independently a C5-C8 alkyl. Values and preferred values of the remainder of the variables are as defined with respect to formula (I).

In certain embodiments of the compounds of formulas (I) through (IV), $R_1$ is —OH, $R_2$ is —OH, and $R_3$, $R_4$, $R_5$, and $R_6$ each is —CH$_3$, or $R_1$ is —OH, $R_2$ is —OCH$_3$, and $R_3$, $R_4$, $R_5$, and $R_6$ each is —CH$_3$. Values and preferred values of the remainder of the variables are as defined with respect to formula (I).

In certain embodiments, the present invention is a poly (deoxybenzoin) homopolymer of any one of the monomers of structural formula (I). Values and preferred values of the variables are as defined with respect to formulas (I) through (IV). In exemplary embodiments, at least one of $R^1$, $R^2$, $R^3$, $R^4$, $R^5$ and $R^6$ is —OH.

In certain embodiments, the present invention is a poly (deoxybenzoin) copolymer of at least one of the monomers of structural formula (I) and at least one additional monomer. In one embodiment, the at least one additional monomer is a compound of formula (V) or formula (VI):

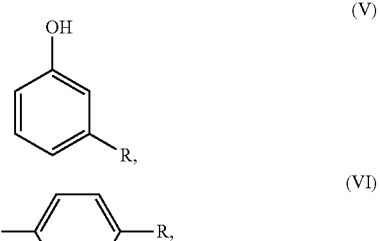

where R, for each occurrence independently, is a C1-C15 alkyl, for example a C1-C6 alkyl or a C1-C3 alkyl, a C2-C15 alkenyl (for example a C2-C6 alkenyl) or a C2-C15 alkynyl (for example a C2-C6 alkynyl). In certain embodiments, R, for each occurrence independently, is a C1-C15 alkyl.

In another embodiment, the at least one additional monomer is selected, for example, from phenol, ethylphenol, phenylphenol, 3-(4-hydroxyphenyl)-1-proponal, 4-hydroxyphenylaceticacid, cardanol, and 3-pentadecylphenol. Values and preferred values of the variables are as defined with respect to formulas (I) through (IV). In exemplary embodiments, at least one of $R^1$, $R^2$, $R^3$, $R^4$, $R^5$ and $R^6$ is —OH; and when $R^1$ and $R^2$ each is —OH, then at least one of $R^3$, $R^4$, $R^5$ and $R^6$ is not —H.

In certain embodiments, the present invention is a method of producing a poly(deoxybenzoin) homopolymer of any one of the monomers of structural formula (I). The method comprises the step of synthesizing a covalent bond between at least two monomers of structural formula (I) to produce the poly(deoxybenzoin) homopolymer. Values and preferred values of the variables are as defined with respect to formulas (I) through (IV). In exemplary embodiments, at least one of $R^1$, $R^2$, $R^3$, $R^4$, $R^5$ and $R^6$ is —OH.

In certain embodiments, synthesizing the covalent bond between the at least two monomers of structural formula (I) includes contacting the at least two monomers of structural formula (I) with an enzyme. Exemplary embodiments of the enzyme include a heme-containing enzyme such as peroxidase (e.g. horse radish peroxidase, soybean peroxidase, manganese peroxidase, chloroperoxidase) or a metalloporphyrin-containing enzyme such as hematin, pegylated hematin, amidated hematin, heamoglobin or myoglobin.

In some embodiments, synthesizing the covalent bond between the at least two monomers of structural formula (I)

includes contacting the at least two monomers of structural formula (I) with chemical oxidation catalyst. Examples of a chemical oxidation catalyst include ferric chloride, ferric sulfate, ammonium persulfate, copper chloride, copper sulfate and potassium ferricyanide.

In certain embodiments, the present invention is a method of producing a poly(deoxybenzoin) copolymer of at least one of the monomers of structural formula (I) and at least one additional monomer. The method comprises the step of synthesizing a covalent bond between at least one monomer of structural formula (I) and at least one additional monomer to produce the poly(hydroxydeoxybenzoin) copolymer. The at least one additional monomer is selected, for example, from phenol, ethylphenol, phenylphenol, 3-(4-hydroxyphenyl)-1-proponal, 4-hydroxyphenylaceticacid, cardanol, and 3-pentadecylphenol. Values and preferred values of the variables are as defined with respect to formulas (I) through (IV). In exemplary embodiments, at least one of $R^1$, $R^2$, $R^3$, $R^4$, $R^5$ and $R^6$ is —OH; and when $R^1$ and $R^2$ each is —OH, then at least one of $R^3$, $R^4$, $R^5$ and $R^6$ is not —H.

In some embodiments, synthesizing the covalent bond between the at least one monomer of structural formula (I) and the at least one additional monomer includes contacting the at least one monomer of structural formula (I) and the at least one additional monomer with an enzyme. Exemplary embodiments of the enzyme include a heme-containing enzyme such as peroxidase (e.g. horse radish peroxidase, soybean peroxidase, manganese peroxidase, chloroperoxidase) or a metalloporphyrin-containing enzyme such as hematin, pegylated hematin, amidated hematin, heamoglobin or myoglobin.

In some embodiments, synthesizing the covalent bond between the at least one monomer of structural formula (I) and the at least one additional monomer includes contacting the at least one monomer of structural formula (I) and the at least one additional monomer with a chemical oxidation catalyst. Examples of a chemical oxidation catalyst include ferric chloride, ferric sulfate, ammonium persulfate, copper chloride, copper sulfate and potassium ferricyanide.

In a particular embodiment, the present invention is an article of manufacture, comprising a poly(hydroxydeoxybenzoin) homopolymer of any one of the monomers of structural formula (I). Values and preferred values of the variables are as defined with respect to formulas (I) through (IV). In exemplary embodiments, at least one of $R^1$, $R^2$, $R^3$, $R^4$, $R^5$ and $R^6$ is —OH.

In another embodiment, the present invention is an article of manufacture, comprising a poly(hydroxydeoxybenzoin) copolymer of at least one of the monomers of structural formula (I) and at least one additional monomer. The at least one additional monomer is selected, for example, from phenol, ethylphenol, phenylphenol, 3-(4-hydroxyphenyl)-1-proponal, 4-hydroxyphenylaceticacid, cardanol, and 3-pentadecylphenol. Values and preferred values of the variables are as defined with respect to formulas (I) through (IV). In exemplary embodiments, at least one of $R^1$, $R^2$, $R^3$, $R^4$, $R^5$ and $R^6$ is —OH; and when $R^1$ and $R^2$ each is —OH, then at least one of $R^3$, $R^4$, $R^5$ and $R^6$ is not —H.

The flame retardant materials of the present invention can be used in bulk or as an additive for other polymers to impart or improve their heat resistance and flame retardancy. The polymer obtained is soluble in common organic solvents and can be coated on to various surfaces including fibers and fabric. Processing could also be done by blending these flame resistant ingredients into the bulk, for example, with an injection molding machine.

Exemplary monomers of the present invention are shown in FIG. 1. The length of the alkyl chains in structures 3 and 4 can be tailored to improve solubility and processability of these materials.

In yet other embodiments of the present invention, the co-polymerization of the phenolic monomers of formula (I) can be extended to several naturally-occurring phenols and substituted phenols not limited to p-phenyl phenol, p-ethyl phenol and cardanol.

Polymerization reactions of the present invention can be carried out in combination of water and other polar solvents such as ethanol, methanol, dimethyl sulfoxide (DMSO) isopropanol, dimethylformamide, dioxane, acetonitrile, and diethyl ether, as well as mixture of solvents. Homopolymers or copolymers can also be synthesized by carrying out the polymerization at elevated temperatures (at 60-80° C.) solvent-free conditions when one or more of the compounds have melting points in the range of 40-60° C.

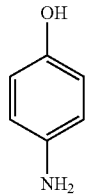

(VII)

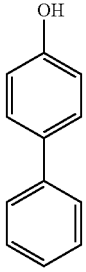

(VIII)

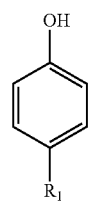

(IX)

It is an object of the present invention to describe a novel enzymatic method for the synthesis of flame retardant polymers based on substituted polyphenols with starting monomers having structural formulae (VII-IX) shown above, where R1 is selected from —COOH, $C_1$-$C_5$COOH, and $C_1$-$C_5$COOCH$_3$. Here $R_1$—CH$_2$COOH is hydroxyphenylacetic acid (HPA) and CH$_2$COOCH$_3$ is methoxyphenylacetic acid (MHPA). It is another object of the present invention that the above polymerization can be carried out in a combination of water and other polar solvents such as ethanol, methanol, dimethylsufoxide, isopropanol, dimethylformamide, dioxane, acetonitrile, diethylether as well as mixture of any of these solvents. It is an object of the present invention to describe a novel oxidative polymerization method using potassium ferricyanide for the synthesis of flame retardant polymers based on substituted polyphenols with starting monomers having structural formulae (VII-IX). It is another object of the present invention that the oxidative polymerization reactions can be carried out in a completely aqueous environment under high pH conditions for the synthesis of flame retardant polyphenols. It is an object of the present invention to describe a novel biomimetic method using iron-N,N'-ethylenebis(salicylideneamine) [iron salen] as the catalyst for the synthesis of flame retardant polymers based on substituted polyphenols with starting monomers having structural formulae (VII-IX). It is another object of the present invention that the polyphenols synthesized using iron salen are very processable and partially or completely soluble. It is yet another object of the present invention that polyphenols synthesized from monomers with structural formulae (VII-IX) are thermally very stable with very high char yields at 800° C. It is yet another object of the present invention that the polyphenols synthesized from monomers with structural formulae (VII-IX) have low heat release capacities in the range of 10-100 J/gK and can be classified as ultra-high fire retardant materials.

TABLE 1

Summary of TGA and PCFC results for p-substituted polyphenols

| Compound | Heat Release Capacity (J/gK) | Total Heat Release (KJ/g) | Char Yield (%) |
| --- | --- | --- | --- |
| Poly(p-aminophenol) | 39 | 3.2 | 51.00 |
| Poly(MHPA) | 51 | 2.8 | 31.00 |
| Poly(HPA) | 12 | 1.5 | 43.10 |
| Poly(p-phenylphenol) | 98 | 5.2 | 57.15 |

It is an object of the present invention that the polyphenols can be used in synergistic combinations with titania, silica or other meso/nano-particulate fillers as well organically modified forms of the fillers for synergistic performance in polymer blends. Synergists are synthesized using chemical covalent functionalization or physical adsorption of the polyphenols on the surface of the meso/nanoparticles. It is yet another object of the present invention that flame retardant polyphenol-$TiO_2$ synergists can be prepared using enzymatic in-situ polymerization of acid functionalized phenol monomers, namely HPA and Hydroxy propyl phenol (HPP) using peroxidases on the $TiO_2$ surface. It is yet another object of the present invention that polyphenol-$TiO_2$ synergists have high char forming capability (>50%) and low heat release capacities (<100 J/gK). It is yet another object of the present invention that polyphenols can be used in combination with organically modified nanoclays for efficient flame retardant performance. It is yet another object of the present invention that polyphenol-TiO2 and polyphenol/nanoclay synergistic combinations are less-toxic environment friendly alternative approaches in place of commonly used metal oxide-halogenated flame retardant synergists. It is yet another object of the present invention that these all of the synthesized polyphenols and synergists can be used in bulk or as an additive for other polymers to impart or improve their heat resistance and flame retardancy. It is yet another object of the present invention that polycardanol can be used as a flame retardant additive to polyolefins, namely polyethylene and polypropylene reins to decrease the overall peak heat release rate, total heat release and the heat release capacity of the compounded blend. It is yet another object of the present invention that the compounding of polyphenol based flame retardant additives and synergists can be incorporated into polymer resins using batch or continuous mixers. It is yet another object of the present invention that the use of polyphenols as flame retardant additives can be extended to other commodity and engineering plastic resins including polystyrene, polymethylmethacrylate, epoxies, polyethyleneterephthalate, polyamides, polyimides, polyisobutylene and acrylonitrile-butadiene-styrene. It is yet another object of the present invention that synergistic combinations of polyphenol with titania, silica or other meso/nano-particulate fillers can be used as flame retardant fillers in commodity and engineering plastic resins including polystyrene, polymethylmethacrylate, epoxies, polyethyleneterephthalate, polyamides, polyimides, polyisobutylene and acrylonitrile-butadiene-styrene.

EXEMPLIFICATION

Example 1

Exemplary Monomers of the Invention and Methods of Analyzing Flame Retarding Properties The polymerization of BHDB (BHDB is compound 1 in FIG. 1) was done using enzymes in a solvent system having up to 20% organic medium. The reaction can be performed in a variety of organic reaction media as a co-solvent including dimethylformamide, dimethylsulfoxide, ethanol and 2-propanol. Hydrogen peroxide was used to initiate the polymerization reactions. The products were dialyzed to remove unreacted monomers. The final product was obtained as a powder after rotary evaporation under low pressure or lyophilization.

Figure 2:
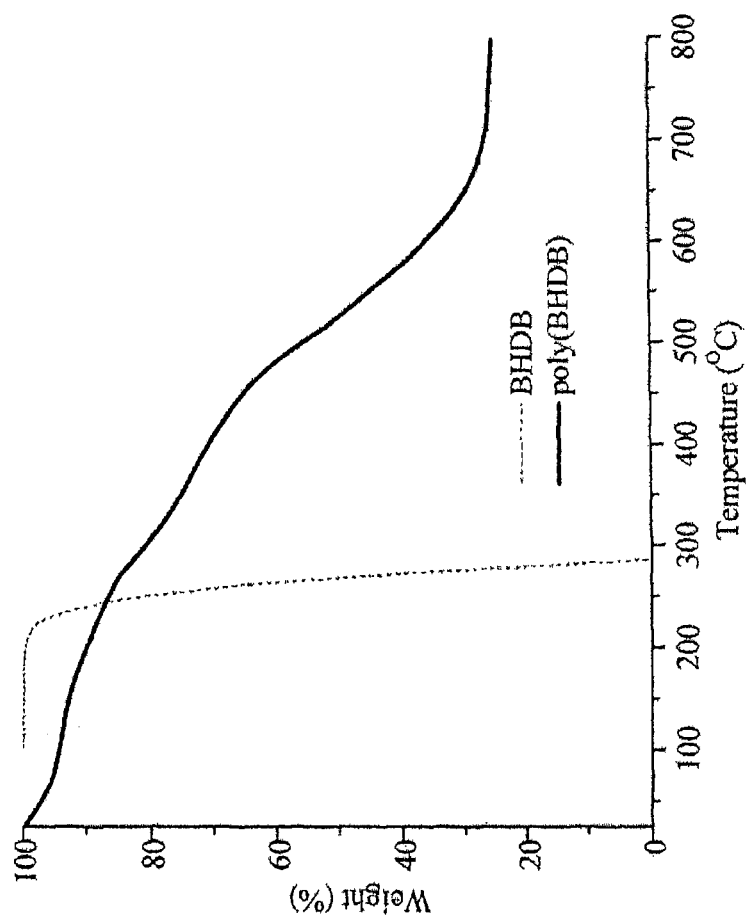
FIG. 2 is a plot showing thermogravimetric analysis data for the monomeric BHDB (4-methoxy-4'-hydroxydeoxybenzoin) and its polymer.

Quantitative measurement of mass change in monomeric and polymeric materials described herein, associated with transition and thermal degradation, was measured using thermo gravimetric analysis (TGA). For example, TGA data for the monomeric BHDB and its polymer is shown in FIG. 2. (The polymerization was accomplished by employing horseradish peroxidase (HRP).)

The polymerization of MHDB (MHDB is compound 2 in FIG. 1) was done using enzymes in a solvent system having up to 20% organic medium, maintained at a pH range of 8-9. Hydrogen peroxide was used to initiate the polymerization reactions. The products were dialyzed to remove unreacted monomers. The final product was obtained as a powder after rotary evaporation under low pressure or lyophilization.

Figure 3:
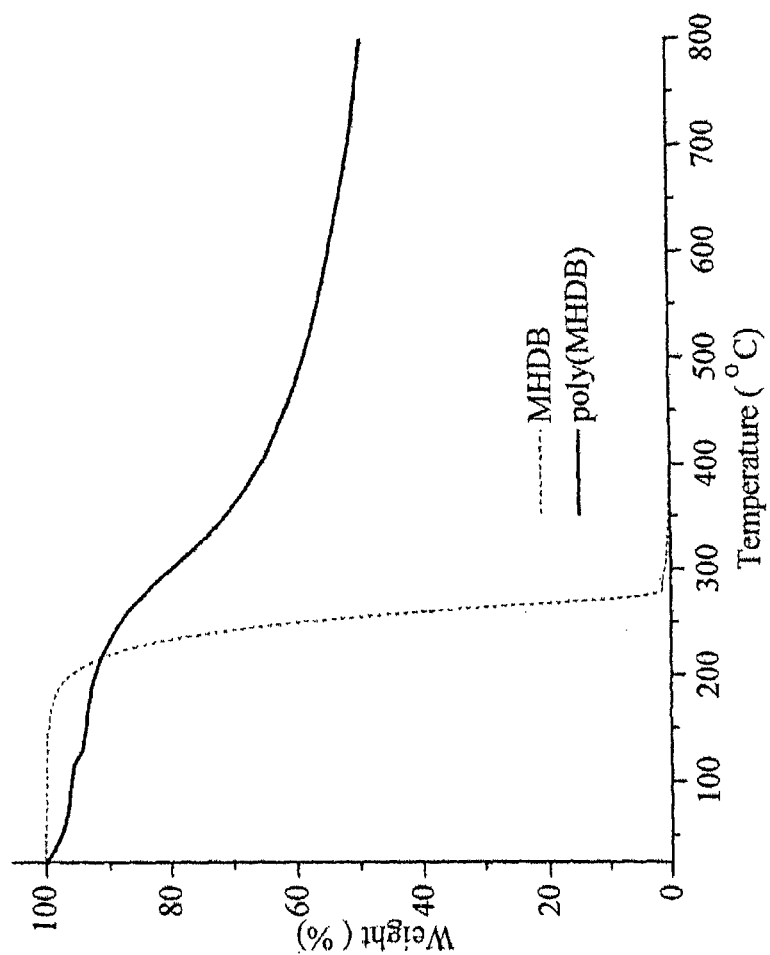
FIG. 3 is a plot showing thermogravimetric analysis data for the monomeric MHDB (4,4'-bishydroxydeoxybenzoin) and its polymer.

Quantitative measurement of mass change in monomeric and polymeric materials described herein, associated with transition and thermal degradation, was measured using TGA. For example, TGA data for the monomeric MHDB and its polymer is shown in FIG. 3. (The polymerization was accomplished by employing HRP)

In yet other embodiments, the present invention is a method of co-polymerization of BHDB and MHDB monomers with phenol. The co-polymerization was done using enzymes in up to 20% organic medium, maintained at a near neutral pH 7 to pH 8. The reaction can be performed in a variety of organic reaction media as a co-solvent including dimethylformamide, dimethylsulfoxide, ethanol and 2-propanol. The use of enzyme was in catalytic amounts, i.e. about 2-3 mg for a 10 ml of the reaction mixture. Hydrogen peroxide was used to initiate the polymerization reactions. The ratio of the phenol co-monomer was varied from 1:1 to 1:10 with that of the BHDB/MHDB monomer. Table 2 summarizes the heat release capacities of homopolymers and copolymers based on BHDB and MHDB monomers.

TABLE 2

Char yield and Heat Release capacities of BHDB and MHDB polymers/copolymers with varying ratios of phenol PCFC (Pyrolysis rate 5° C./s and char yields measured at 900° C.).

| Compound | Heat Release Capacity (J/gK) | Total Heat Release (KJ/g) | Char yield (%) |
|---|---|---|---|
| Poly (BHDB) | 15 | 3.3 | 51.9 |
| Poly (MHDB) | 19 | 2.8 | 40 |
| Poly (phenol) | 42 | 3.1 | 47.7 |
| Poly(BHDB:phenol) - 1:1 | 30 | 4.5 | 58.7 |
| PoJy(BHDB:phenol) - 1:5 | 37 | 3.9 | 53.8 |
| Poly(BHDB:phenol) - 1:10 | 55 | 7.2 | 56 |
| Poly(MHDB:phenol) - 1:1 | 46 | 6.8 | 55.1 |
| Poly(MHDB:phenol) - 1:5 | 46 | 7.4 | 54.7 |
| Poly(MHDB:phenol) - 1:10 | 53 | 7.6 | 59.1 |

Example 2

Structural and Thermal Characterization of Poly(Deoxybenzoin) Polymers of the Present Invention After the synthesis of poly(hydroxydeoxybenzoin)s based on substituted phenol monomers, structural and thermal characterization was done as follows. The following protocol describes the methods and experimental parameters used to characterize the synthesized polymers.

The molecular weight of the polymers formed using this biocatalytic polymerization was analyzed using an Agilent 1100 series Gel Permeation Chromatography system. The compounds were dissolved in dimethylformamide (mobile phase) and were run at a 1 ml/min flow rate. The eluted volume was monitored using a Refractive Index (RI) detector. The thermal stability of the monomeric and polymeric samples was analyzed using a thermogravimetric analyzer (TGA Q50, V6.7). Approximately 10 milligrams of the samples were weighed in platinum pans and heated up to 750° C. at a rate of 10° C./min. All the samples were run under a constant air flow of 10 ml/min. Pyrolysis Combustion Flow calorimetry was done at Trace Technologies LLC. Samples were heated at 5° C./s until decomposition was complete (maximum 900° C.). Typical sample sizes are about 5-10 mg. The samples were tested in triplicate and the results averaged.

Example 3

Polymerization of BHDB

Figure 4:
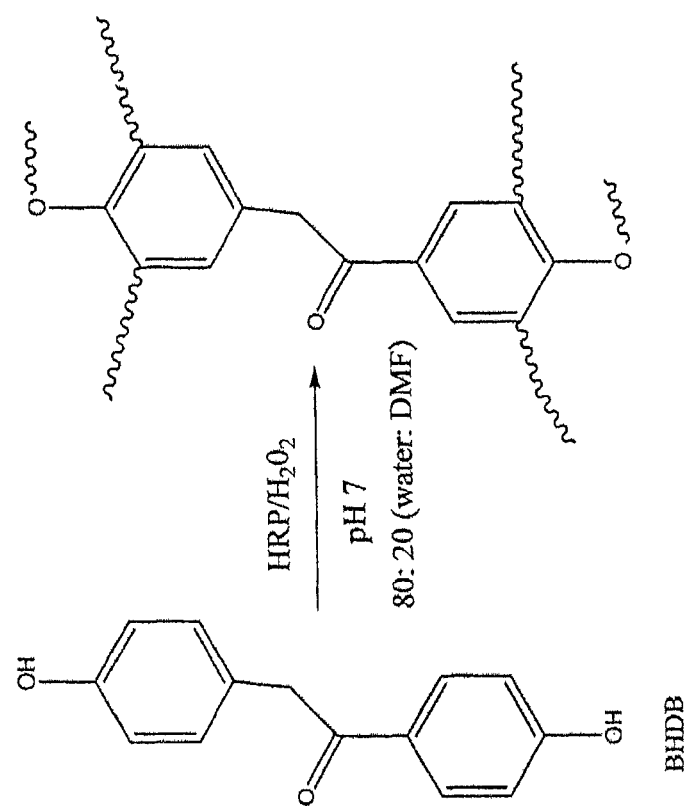
FIG. 4 is an illustration of a proposed synthetic scheme for polymerization of BHDB.

Polymerization of BHDB was carried out in mixtures of pH 7 phosphate buffer and DMF (80:20), as shown in the synthetic scheme depicted in FIG. 4. The insolubility of BHDB in water necessitated the use of an organic solvent dimethyl formamide (DMF) in small amounts. The reaction mixture was prepared by the addition of 5 mM BHDB to the buffer solution, followed by the addition of 3 mg of the enzyme. The polymerization was initiated by the addition of 5 mM, 0.3% Hydrogen Peroxide in small aliquots over a period of one hour. The polymerization was complete in 3 hours. After the reaction was complete, the reaction mixture was dialyzed in 1000 Mol wt dialysis bags against water. The synthesized polymeric forms of BHDB had a number average molecular weight ranging from 3000-7000 Da, as shown in Table 3. Thermal characterization was done using the procedure described in Example 2.

Example 4

Polymerization of MHDB

Figure 5:
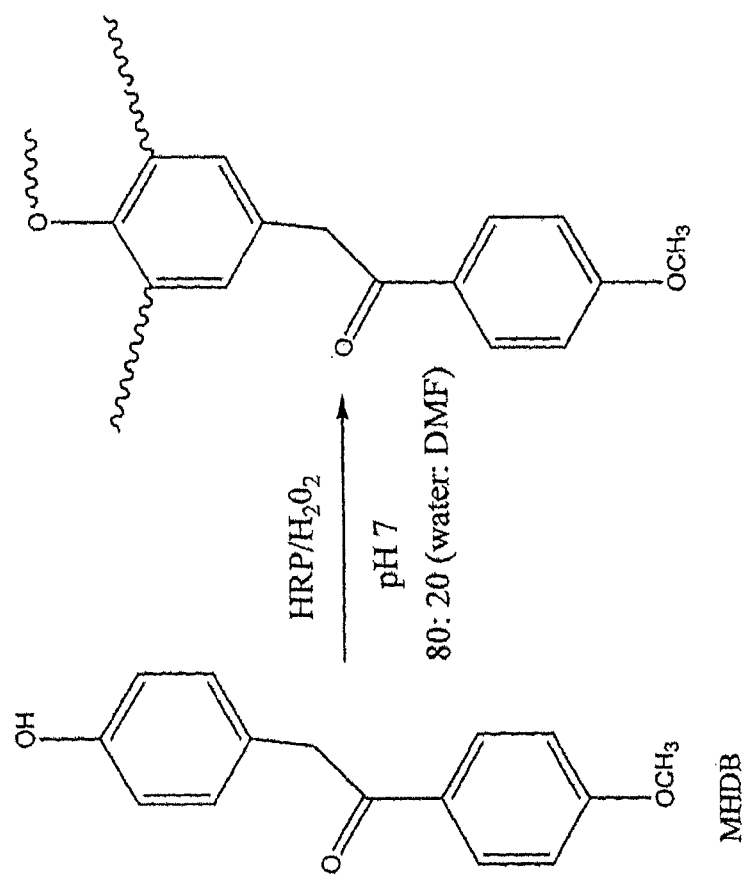
FIG. 5 is an illustration of a proposed synthetic scheme for polymerization of MHDB.

Polymerization of MHDB was carried out in mixtures of pH 8 phosphate buffer and DMF (80:20) according to a scheme depicted in FIG. 5. The insolubility of MHDB in water necessitated the use of an organic solvent dimethyl formamide (DMF) in small amounts. The reaction mixture was prepared by the addition of 5 mM MHDB to the buffer solution, followed by the addition of 3 mg of the enzyme. The polymerization was initiated by the addition of 5 mM, 0.3% Hydrogen Peroxide in small aliquots over a period of one hour. The polymerization was complete in 3 hours. After the reaction was complete, the reaction mixture was dialyzed in 1000 Mol wt dialysis bags against water. The synthesized polymeric forms of MHDB had a number average molecular weight ranging from 3000-7000 Da, as shown in Table 3. Thermal characterization was done using the procedure described in Example 2.

Example 5

Co-Oligomerization of MHDB and BHDB with Phenol

Figure 6:
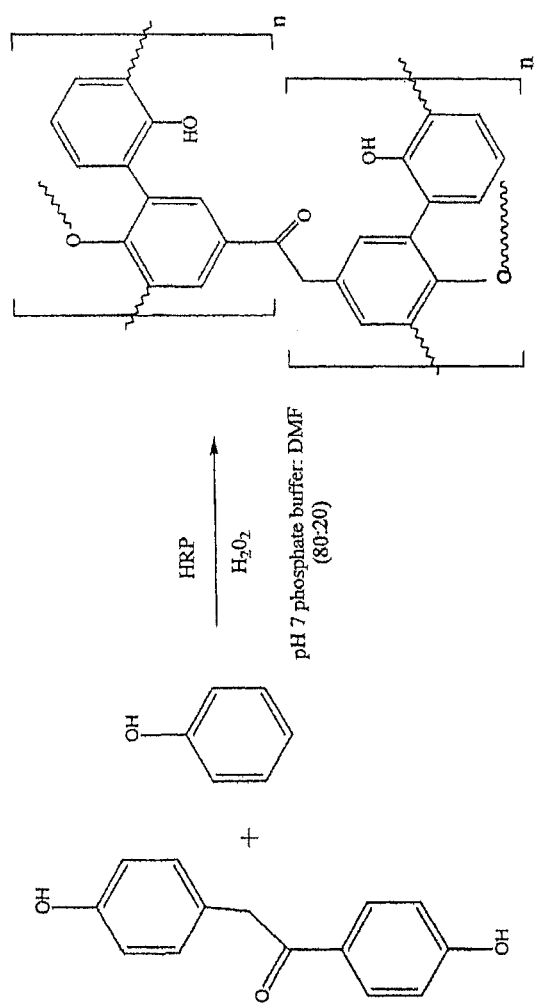
FIG. 6 is an illustration of a proposed scheme for co-polymerization of BHDB and phenol employing HRP as the enzyme.

Co-oligomerization of MHDB and BHDB with phenol was carried out in mixtures of pH 7 phosphate buffer and DMF (80:20) according to a scheme depicted in FIG. 6. The insolubility of BHDB and MHDB in water necessitated the use of an organic solvent dimethyl formamide (DMF) in small amounts. Also, the addition of phenol increased the solubility of the monomer in the reaction mixture. The reaction mixture was prepared by the addition of 5 mM phenol and 5 mM MHDB to the buffer solution, followed by the addition of 3 mg of the enzyme. The polymerization was initiated by the addition of 5 mM, 0.3% Hydrogen Peroxide in small aliquots over a period of one hour. The polymerization was complete in 3 hours. After the reaction was complete, the reaction mixture was dialyzed in 1000 Mol wt dialysis bags against water. The synthesized polymeric forms of MHDB had a number average molecular weight ranging from 6000-10000 Da, as shown in Table 3. Thermal characterization was done using the procedure described in Example 2.

TABLE 3

GPC analysis of deoxybenzoin and deoxybenxoin/phenol copolymers

| Molar Ratios | BHDB-co-Phenol | | MHDB-co-Phenol | |
|---|---|---|---|---|
| (Benzoins:Phenol) | Yield (%) | Mn (Da) | Yield (%) | Mn (Da) |
| 100:0 | 68 | 5400 | 65 | 4800 |
| 99:1 | 75 | 6220 | 73 | 5440 |
| 95:5 | 81 | 8400 | 77 | 7040 |
| 90:10 | 90 | 11360 | 84 | 9650 |
| 80:20 | 65 | 10340 | 54 | 6600 |

Example 6

Chemical Oxidative Polymerization of Cardanol in Water

Figure 7:
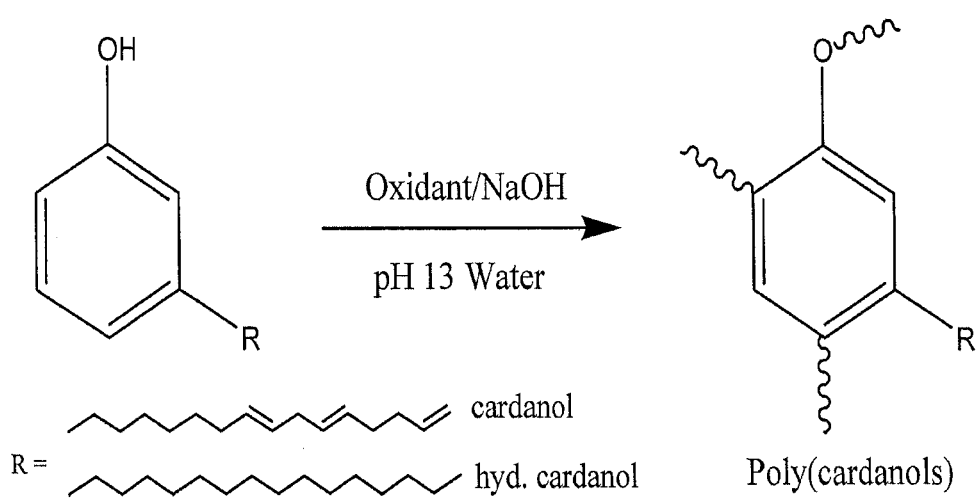
FIG. 7 is a FTIR-ATR spectrum of the polymer synthesized according to the procedures of Example 6.
Figure 8:
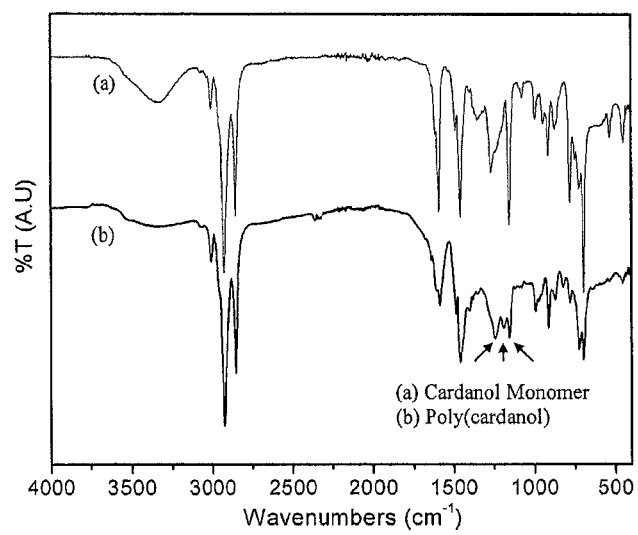
FIG. 8 is a proposed reaction scheme for poly(cardanols/hydrogenated cardanol) synthesis.

The procedure described herein was for the chemical oxidative polymerization of cardanol in water, and is represented in FIG. 7. 0.30 g of Cardanol (1 mmol) was dissolved in 100 mL of water containing sodium hydroxide (2 g, 50 mmol) maintained at 50° C. Potassium Ferricyanide (0.658 g, 2 mmol) was then added to the solution and the mixture was stirred at 1100 rpm for 6 hours. The polymer (brown solid) was filtered after salting out with sodium chloride (5.84 g, 0.25 mol) followed by extensive washing with water to remove any residual sodium chloride. The filtered product was then washed with hexanes in a Soxhlet extractor for 24 hours. Similarly, hydrogenated cardanol was also polymerized using a similar procedure at slightly elevated temperatures of 60° C. for 8 hours. The resulting products were characterized using procedures described in Example 2. The FTIR-ATR spectrum of the synthesized polymer, as shown in FIG. 8 is characteristic of a C—C/C—O—C coupled polyphenol.

Example 7

Enzymatic Polymerization of p-Substituted Phenol

Figure 9:
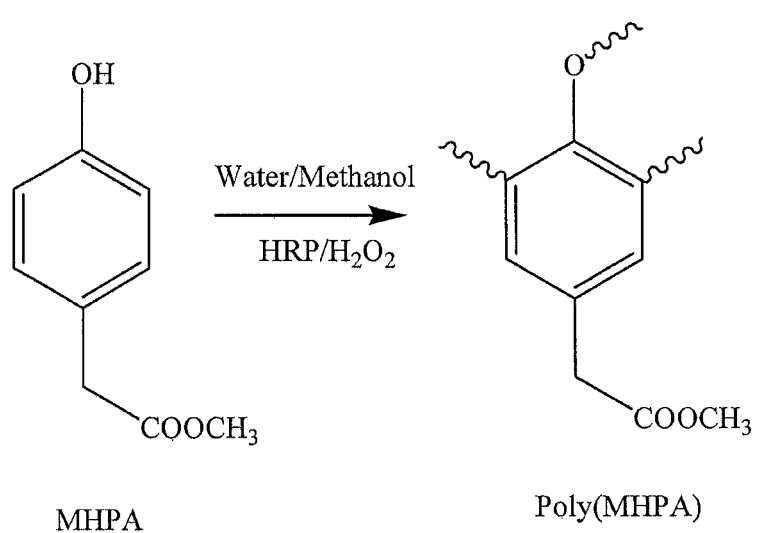
FIG. 9 is a proposed reaction scheme for enzymatic polymerization of MHPA.

The procedure described herein was the enzymatic polymerization of p-substituted phenol MHPA, as represented in FIG. 9. MHPA (100 mmol, 0.166 g) was dissolved in solvent mixture containing water (7 ml) and ethanol (3 ml). The solution was sonicated to completely dissolve the monomer. HRP (10 mg in 1 ml of water, 0.4 ml) was added followed by the addition of hydrogen peroxide (H2O2, 3% in water, 1 ml). The reaction mixture was stirred followed by precipitation and removing unreacted monomer with dialysis membrane for 24 hours. The obtained precipitate was centrifuged and dried under vacuum overnight and characterized using techniques described in Example 2.

Example 8

Oxidative Polymerization of p-Aminophenol

Figure 10:
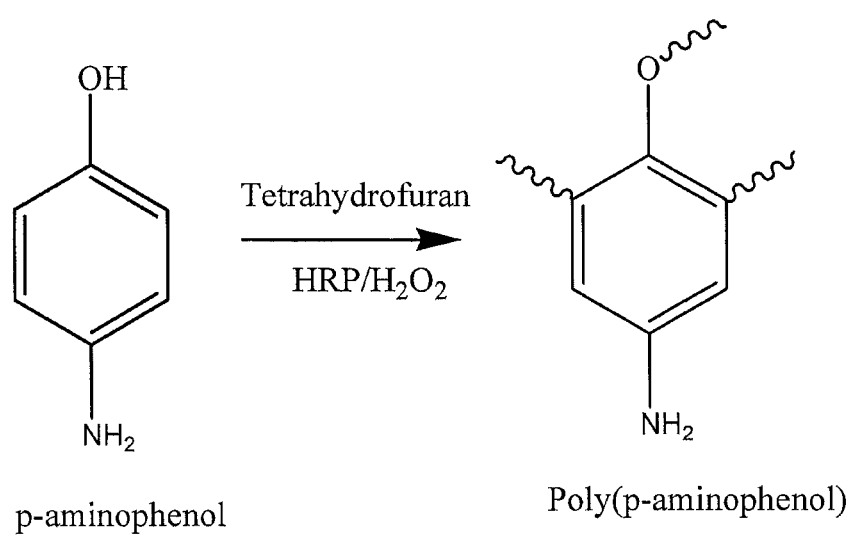
FIG. 10 is a proposed reaction scheme for oxidative polymerization of p-aminophenol using iron salen.

The procedure described herein was the oxidative polymerization of p-substituted polyphenol namely p-aminophenol, as represented in FIG. 10. To a solution of phenolic monomer (1 mmol) in tetrahydrofuran (5 mL), Fe-Salen (10 mg) was added and the reaction mixture was stirred for 5 minutes. The polymerization was then initiated by incremental addition of a stoichiometric amount of hydrogen peroxide (3% aq. solution, 1.8 ml, 1 mmol) dropwise over a period of 10 minutes. After complete addition of $H_2O_2$, the reaction mixture was allowed to continue for another 10 hours at room temperature. The solvent was evaporated under reduced pressure and the residue was then washed thoroughly with 0.1M HCl solution, followed by soxhlet extraction in methanol for 24 hours to remove un-reacted reactants. The product was then dried under vacuum for all further characterization. Flammability analysis using PCFC indicate that poly(p-aminophenol) exhibits low heat release capacities in the range of 150-200 J/gK.

Example 9

Surface Modification of $TiO_2$ Using p-Substituted Polyphenols

The procedure described herein was surface modification of $TiO_2$ using p-substituted polyphenols like HPA. After successful synthesis of poly(HPA), it can be electrostatically bound to the hydroxyl entities on the $TiO_2$ surface between pH 4.5 to 6. This is followed by thorough washing of the free polyphenol using dimethylformamide followed by centrifuging and vacuum drying the final product. Up to 10% functionalization of the $TiO_2$ surface was achieved using this method.

Example 10

Polycardanol/polyolefin Flame Retardant Blends

Ortho, meta and para substituted phenols was synthesized using chemical, enzymatic and biomimetic polymerization techniques can be used as flame retardant additives for any commodity, industrial or high performance plastics. This example describes the compounding of polycardanol into polyethylene (PE) to make polyethylene/polycardanol blends for effective fire performance. Polycardanol was blended into PE using a CW brabender type 6 mixer. The temperature of the mixing barrel was maintained at 185° C. 30 g of total compound is loaded into the barrel in each batch and a constant mixing speed of 60 rpm was used to achieve optimum blending. End of mixing is monitored by observing the stabilization in torque of the mixer which is usually achieved after 10 minutes. Several blend ratios using 1, 5, 10 and 15% of the flame retardant additive by weight was compounded into the virgin polymer. After compounding, thermal analysis of these blends are done using TGA and PCFC. Table 3 shows summary of char yields and heat release capacities of polycardanol-polyolefin blends.

TABLE 4

Summary of PCFC results of Polyolefin/Polycardanol blends

| Polymer | THR (KJ/mol) | Char Yield (%) | HRC (J/gK) | % Decrease in HRC |
|---|---|---|---|---|
| LDPE | 40.3 | 0 | 1375 | — |
| LDPE + 1 PC | 40.2 | 2.2 | 1310 | 4.7 |
| LDPE + 5 PC | 38.6 | 4.5 | 1254 | 8.8 |
| LDPE + 10 PC | 37.2 | 6.2 | 999 | 27.4 |
| LDPE + 15 PC | 38.6 | 4.8 | 1070 | 22.2 |
| PP | 40.1 | 0 | 1250 | — |
| PP + 1 PC | 39.8 | 2.2 | 1081 | 13.52 |
| PP + 5 PC | 37.8 | 3.9 | 990 | 20.8 |
| PP + 10 PC | 35.8 | 9.4 | 910 | 27.2 |
| PP + 15 PC | 35.5 | 9.2 | 840 | 32.8 |

LDPE: Lowdensitypolyethylene;
PP: Polypropylene;
PC: Polycardanol

Example 11

Polyolefin/Polyphenol Synergist Blends

Poly(HPA), $TiO_2$ and Polyphenol-$TiO_2$ synergist were be blended into LDPE using the method described in Example 10. Blending ratios of 1, 5 and 10% by weight of the flame retardant was compounded into the virgin polymer. After compounding, thermal analysis of these blends are done using TGA and PCFC. Table 4 shows summary of char yields and heat release capacities of polyphenol/$TiO_2$ synergists-polyolefin blends.

TABLE 5

Summary of PCFC results of Polyolefin/Polyphenol synergist blends
The teachings of all patents, published applications and references
cited herein are incorporated by reference in their entirety.

| Polymer | THR (KJ/mol) | Char Yield (%) | HRC (J/gK) |
|---|---|---|---|
| Neat LDPE | 39.4 | 0 | 1319 |
| Poly(HPA) | 1.5 | 43.00 | 12 |
| $TiO_2$ | — | 100 | — |
| $TiO_2$ and poly(HPA) | — | 87.06 | — |
| LDPE + 1% Poly(HPA) | 42.5 | 2.08 | 1160 |
| LDPE + 5% Poly(HPA) | 41.0 | 2.50 | 1132 |
| LDPE + 10% Poly(HPA) | 39.7 | 4.65 | 1081 |
| LDPE + 1% $TiO_2$ | 42.6 | 1.00 | 1123 |
| LDPE + 5% $TiO_2$ | 39.9 | 2.08 | 1296 |
| LDPE + 10% $TiO_2$ | 37.9 | 7.50 | 1127 |
| LDPE + 1% Synergist | 43.3 | 2.04 | 1121 |
| LDPE + 5% Synergist | 42.1 | 7.60 | 1244 |
| LDPE + 10% Synergist | 39.2 | 8.70 | 1047 |

While this invention has been particularly shown and described with references to example embodiments thereof, it will be understood by those skilled in the art that various changes in form and details may be made therein without departing from the scope of the invention encompassed by the appended claims.

The invention claimed is:

1. A poly(deoxybenzoin) homopolymer of any one of the monomers of structural formula (I):

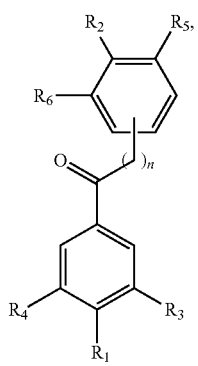

(I)

wherein:
$R^1$, $R^2$, $R^3$, $R^4$, $R^5$ and $R^6$ each independently is selected from —H, —OH, a C1-C8 alkoxy, or a C1-C15 alkyl; and
n is 1, provided that at least one of $R^1$, $R^2$, $R^3$, $R^4$, $R^5$ and $R^6$ is —OH.

2. The homopolymer of claim 1, wherein the monomer of structural formula (I) is represented by a structural formula selected from formulas (II) and (III):

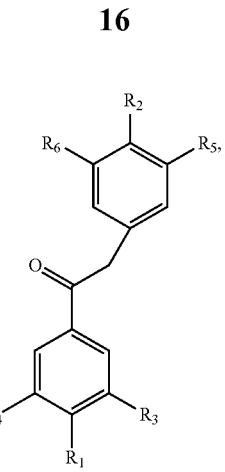

(II)

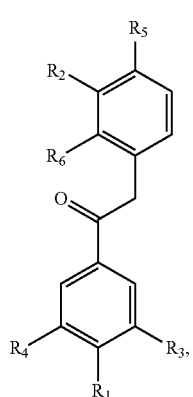

(III)

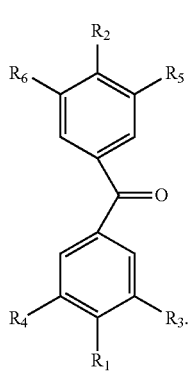

(IV)

3. The homopolymer of claim 1, wherein $R^1$ is —OH and $R^2$ is —OH or —OCH$_3$.

4. The homopolymer of claim 3, wherein $R^3$, $R^4$, $R^5$ and $R^6$ each is independently —H or a C1-C8 alkyl.

5. The homopolymer of claim 1, wherein:
$R_1$ is —OH, $R_3$, $R_4$, $R_5$, and $R_6$ each is independently a C5-C8 alkyl, and $R_2$ is —OH, or —OCH$_3$.

6. The homopolymer of claim 1, wherein:
$R_1$ is —OH, and $R_3$, $R_4$, $R_5$, and $R_6$ each is —CH$_3$, and $R_2$ is —OH or —OCH$_3$.

7. The homopolymer of claim 1, wherein:
$R_1$ is —OH, and $R_3$, $R_4$, $R_5$, and $R_6$ each is —H, and $R_2$ is —OH or —OCH$_3$.

* * * * *